(12) United States Patent
Lian (10) Patent No.: US 8,968,684 B2
(45) Date of Patent: Mar. 3, 2015

(54) MICROPLATES, REACTION MODULES AND DETECTION SYSTEMS

(76) Inventor: Bin Lian, Portland, OR (US)

( * ) Notice: Subject to any disclaimer, the term of this patent is extended or adjusted under 35 U.S.C. 154(b) by 979 days.

(21) Appl. No.: 13/096,914

(22) Filed: Apr. 28, 2011

(65) Prior Publication Data

US 2012/0276541 A1    Nov. 1, 2012

(51) Int. Cl.
*B01L 7/00* (2006.01)
*G01N 21/64* (2006.01)
*G01N 35/02* (2006.01)
*G01N 35/04* (2006.01)

(52) U.S. Cl.
CPC .............. *B01L 7/52* (2013.01); *B01L 2200/021* (2013.01); *B01L 2200/025* (2013.01); *B01L 2300/042* (2013.01); *B01L 2300/044* (2013.01); *B01L 2300/0654* (2013.01); *B01L 2300/0663* (2013.01); *B01L 2300/0829* (2013.01); *B01L 2300/0851* (2013.01); *B01L 2300/0858* (2013.01); *B01L 2300/123* (2013.01); *B01L 2300/168* (2013.01); *B01L 2300/1827* (2013.01); *G01N 21/6452* (2013.01); *G01N 35/026* (2013.01); *G01N 2035/042* (2013.01)
USPC ........................................... 422/552; 422/566

(58) Field of Classification Search
CPC ..................... B01L 2300/18; B01L 2300/0851
USPC ............................................. 435/303.1, 91.2
See application file for complete search history.

(56) References Cited

U.S. PATENT DOCUMENTS

| | | |
|---|---|---|
| 5,459,300 A | 10/1995 | Kasman |
| 6,015,534 A | 1/2000 | Atwood |
| 6,232,114 B1 | 5/2001 | Coassin |
| 7,074,367 B2 | 7/2006 | Lurz et al. |
| 2004/0086927 A1 * | 5/2004 | Atwood et al. ................ 435/6 |
| 2004/0258568 A1 * | 12/2004 | Lurz et al. ..................... 422/99 |
| 2010/0055743 A1 | 3/2010 | Banerji |

* cited by examiner

*Primary Examiner* — Natalia Levkovich
(74) *Attorney, Agent, or Firm* — Baumgartner Patent Law; Marc Baumgartner (57) ABSTRACT

Microplates, reaction modules and optical detection systems for chemical and/or bio-chemical reactions including polymerase chain reactions.

6 Claims, 6 Drawing Sheets

MICROPLATES, REACTION MODULES AND DETECTION SYSTEMS

BACKGROUND OF THE INVENTION

1. Field of the Invention

The present invention relates generally to a device for temperature controlled chemical and/or bio-chemical reactions. More particularly, the present invention relates to real-time detection of Polymerase Chain Reaction (PCR).

Many applications such as microbiology, genetic disease diagnostics, forensic, food science only have small amount of DNA for analysis, which is very difficult to detect. Polymerase chain reaction became a very valuable technique which is capable of producing large amount of copied DNA fragments from minute amounts of DNA samples, for both sequencing and genotyping applications.

During PCR process, the solution undergoes temperature cycles to create copy of the original DNA fragment in each cycle. Each temperature cycle consists of generally three steps: (1) Denaturation (~95° C.); (2) Annealing (~50° C.); (3) Extension/Elongation (~70° C.).

Two important factors are critical to the PCR tests: the ability for the samples in the microplate holding the samples to reach their set point temperature quickly so the whole test can be completed in reasonable time frame, and the ability of the reaction module to maintain temperature uniformity among array of microwells for each set point temperature.

2. Description of the Related Art

For purposes of screening, statistical analysis, or large scale assay project, it is highly desirable to process many samples at the same time under similar test conditions. Most common PCR sample tray (microplate) is constructed with a solid top frame holding many microwells arranged in 2-D pattern, such as 12×8 (a total of 96 wells) format, 24×16 (a total of 384 wells) format. The microwell usually has conical profile (FIG. 8A-B) for ease of insertion and removal from the thermal block, in which temperature is controlled, as described in U.S. Pat. No. 6,015,534 (Atwood, The Perkin-Elmer Corporation). The thermal block has matching machined conically shaped cavities to accommodate the sample wells. The thermal block is usually attached to a thermoelectric module for controlled heating and cooling, or it has channels machined near the bottom to allow heating or cooling fluid to pass through to realize temperature control.

The thermal block of such design is fairly complex and expensive to make, the microplate also has to have its conical shaped wells matched perfectly to the cavity geometry to get the uniform heating/cooling desired. The other drawbacks include: heat transfer to the sample could take a long time since it has to travel substantial distance upwards from the bottom of the thermal block to reach top portion of the microwell; this also introduces non-uniform heating/cooling in the sample solution from top to bottom since the bottom part will reach the set point temperature much earlier than the top portion. Such design is also far from optimal from optical performance standpoint, since both excitation and emission light have to travel through the depth of the microwell which results in significant signal attenuation.

There have been incremental improvements over such design. One example, as described in U.S. Patent Application Pub. No. 2010/0055743 A1 (Banerji, Bio-Rad Laboratories, Inc.), the thermal block was trimmed to reduce thermal mass to improve response time. Such incremental improvement came with extra costs for more complex thermal block design and manufacturing. It didn't resolve the non-uniform heating/cooling issue at different depths of the microwell.

Another design available in the market is glass capillary tube design. Slender glass tubes loaded with sample solutions are placed onto the thermal control module in circular pattern, convective heating/cooling is utilized by blowing temperature controlled air stream to this glass tube ring array. The glass tube has to be very thin to obtain good heat transfer which makes it fairly fragile; it also has to have small cross-section for the same reason, which makes it difficult to inject the sample solution. In addition, this method has the challenge of scaling up to accommodate large number of samples.

There have been other ideas to further enhance the PCR thermal module performance. One example was described in U.S. Pat. No. 5,459,300 (Kasman), in which a thermally conductive compliant layer was added between the microplate and the heating surface, with the desire to accommodate various existing microplate bottom geometries (flat, U-shaped, V-shaped). Such compliant layer, even with the addition of thermally conductive fillers, usually has very poor thermal properties compared to metals such as aluminum and copper, and it also introduces additional thermal interface, all these result in slow response time. Furthermore, heat transfer is very sensitive to variation of the thickness of the compliant layer when it is under vertical load, a parameter very difficult to control under such embodiment, resulting in non-uniform heating and response time among microwells. In addition, most microplate designs do not assume heat transfer through microwell bottom, which could further deteriorate the solution's thermal performance.

The other approach, as described in U.S. Pat. No. 7,074,367 (Lurz, et al.), used a static PCR microplate coupled with a sample block, while allowing thermostated blocks (set at different temperatures/profiles) to make contact to its bottom surface. How to effectively make the contact interface thermally optimal (low contact resistance, uniform across the whole surface) is a significant challenge. This solution still suffers the large thermal mass encountered in conventional design, resulting in slow thermal response and long cycle time.

There are other flat bottom microplate designs, one example as described in U.S. Pat. No. 6,232,114 (Coassin, et al., Aurora Bioscience Corporation) to address mainly optical accessibility challenges, other than the thermal response and uniformity problems that the PCR process encountered.

Accordingly, there is a need in the art to establish a device that would address cost, thermal response, and uniformity for the PCR process.

SUMMARY OF THE INVENTION

Embodiments of the invention relate to a microplate, temperature controlled reaction modules and optical detection systems capable of rapidly heating and cooling samples stored in an array of microwells while real-time information about the samples are measured. The unique thin wall microplate and flat bottom design, coupled with distributed load on each well, allow effective heat transfer from the temperature controlled heating/cooling surface while maximizing optical signal generation and collection. Proper embodiments of this invention dramatically reduce plastics material consumption for consumables such as the microplate, improve thermal response and thermal cycle time, reduce sample volume, while saving energy required for each cycle.

A microplate molded from thin sheet of thermally conductive plastics, comprises a planar top frame of substantial flexibility with a plurality of openings which defines microwells hang below the top frame to hold reaction samples. The thickness of the microplate is chosen such that the top frame retains sufficient flexibility, allowing it to deflect locally while under distributed vertical loads. The side wall of the microwell is substantially cylindrical or conical, it shows minimal deformation while load is applied vertically from the top frame, and it transfers the pressure load to the bottom wall. The joining edge between the microwell side wall and the bottom wall is preferably rounded, when vertical load is applied through the side wall, it flattens out slightly towards the bottom wall; this enhances contact area and creates a compression stress to the bottom wall. The bottom of the microwell is substantially planar or gently convex so that when pressure is applied from the side wall, it complies to a temperature controlled surface below to makes intimate contact across its surface.

A temperature controlled reaction module consists of the microplate, a means for clamping to provide uniform distributed loading on individual microwell, and at least one temperature controlled platen whose top surface is substantially planar to provide desired temperature profile(s). The microplate is sealed by a thin and transparent adhesive film. Distributed loading is realized by an elastic layer between the means for clamping and the sealing-film/microplate assembly. In a static system embodiment, the microplate is engaged with one temperature controlled platen surface constantly through the PCR test process, thermal cycling is realized by transitioning the temperature controlled platen surface to different set point temperatures. In a dynamic system embodiment in which multiple temperature controlled platens are provided, horizontal and vertical servo motors are used to transport the microplate assembly to make contact with the top surfaces of these platens.

Optical access could be provided through either the top opening of the microwell or the through the bottom of each microwell depending on the embodiments.

A real-time fluorescent detection system comprises a reaction module encapsulating a microplate, an excitation light source assembly, emission filters assembly, a first surface mirror, an optical lens/imaging sensor assembly, power and control electronics, and an enclosure.

BRIEF DESCRIPTION OF THE DRAWINGS

FIG. 1A-E is a collection of three dimensional and cross-sectional views of a microplate according to the invention. FIGS. 1A and 1B are oblique views of the microplate. FIG. 1D and FIG. 1E are cross-sectional views of one microwell with a planar bottom and one with a slightly convex bottom, along section line A-A as shown in FIG. 1C.

FIG. 8A-B is a cross-sectional view of prior arts.

DETAILED DESCRIPTION OF THE ILLUSTRATED EMBODIMENT

Figures 1A, 1B, 1C, 1D, 1E:
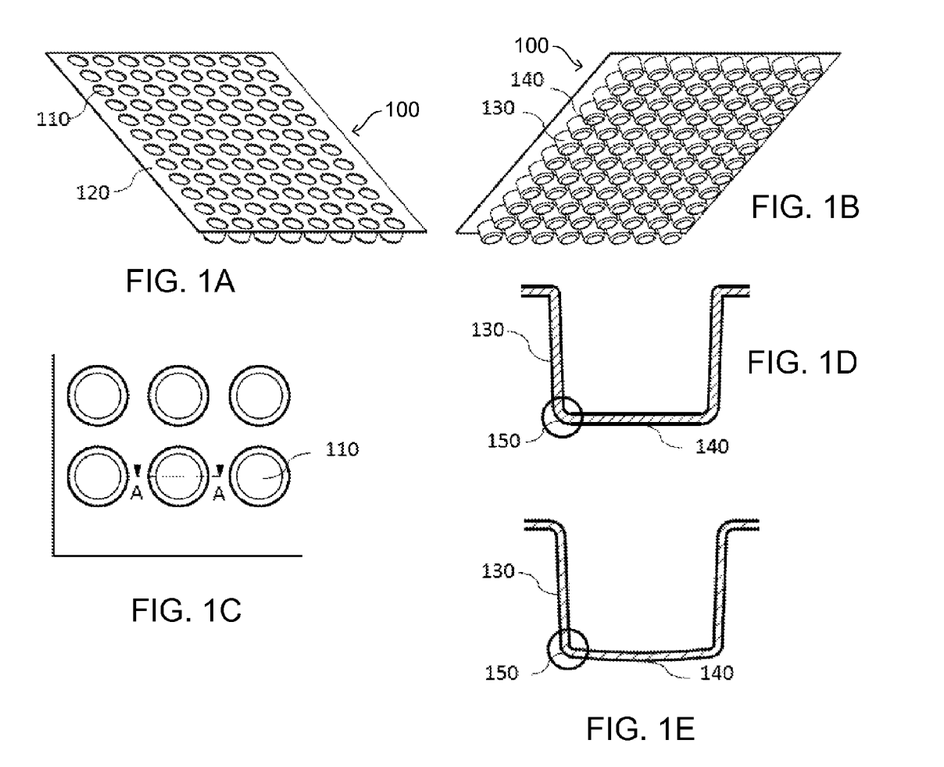

FIG. 1A-E illustrate a microplate 100 of the present invention comprising a planar top frame 120 and a plurality of microwells 110 recessed below the top frame 120. The microplate 100 can be made using any suitable manufacturing techniques, preferably molded from thin sheet of thermally conductive materials. FIG. 1A and FIG. 1B show oblique views of embodiment of the microplate.

The microwell side wall 130 has a profile that is substantially cylindrical or conical; it provides structural support and transfers vertical load to the bottom of the microwell when the vertical load is applied to the top frame 120.

The bottom of the microwell 140 is planar (FIG. 1D) or slightly convex (FIG. 1E) so that when load is applied vertically down the side wall, it presses the microwell bottom wall 140 towards the top surface of temperature controlled heating/cooling platen 230 to makes intimate contact. Bottom edge of the microwell 150 should be rounded, such that when vertical load is applied, it flattens out slightly and creates compression stress on the bottom wall, this further enhances microwell bottom wall contact with the surface below. FIG. 1D shows an embodiment of microwell bottom that is planar, which is mostly suitable for high density microplate format (384 wells, for example) where the well dimension is small. FIG. 1E shows an embodiment in which the microwell bottom is slightly convex, together with rounded edge 150, this creates compression stress on the bottom wall when load is applied vertically along the side wall, this ensures microwell bottom wall tightly contact the top surface of temperature controlled heating/cooling platen 230. Such embodiment is most suitable for designs with larger microwell dimension (96 wells, for example).

The microplate 100 can be manufactured in high volume by any common processes such as thermo forming, vacuum forming, blow molding. It is preferable to keep the microplate thin for optimal heat transfer, and to keep the top frame flexible to allow distributed vertical loads to be applied to individual microwell; however, it should be sufficiently thick to maintain structural integrity of the microwells, so it would not collapse while under vertical load.

The microplate 100 is preferably fabricated from a thermally conductive and chemically inert materials, such as, but not limited to, polypropylene, polystyrene, polycarbonate and the like. If the selected material is optically transparent or translucent, filler such as black pigment can be mixed with the molding compound to make the molded part opaque, reducing the effects of cross talk (optical signal of one cell interfering with neighboring cells). The microplate can be coated on the outer side of the microwell 110 (outer surface of sidewall 130, underside of the bottom wall 140, and outer side of the rounded joining edge 150) and the underside of the top frame 120 with opaque or reflective layer.

The microplate 100 can be made in any formats and patterns, including 96 well format (12×8), 384 well format (24×

16), or even 1536 wells format (48×32). Microplate lateral dimensions can be varied as well as the wall thickness and microwell profile.

Figure 2:
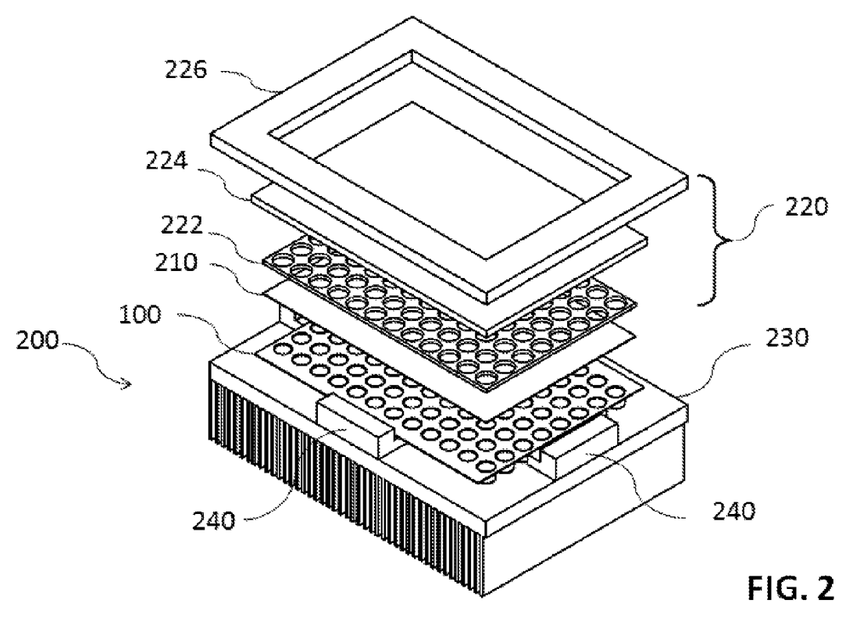
FIG. 2 is a three dimensional exploded view of a reaction module embodiment according to the invention. The means for clamping at the top, microplate assembly and the heating/cooling platen are mechanically engaging during the full length of temperature cycling of the PCR test.

FIG. 2 illustrates an oblique exploded view of one embodiment of reaction module 200 in which the bottom underside of the microwells of microplate 100 is engaged with the top surface of temperature controlled heating/cooling platen 230 statically throughout the whole PCR test process. Preferably the reaction module 200 includes a microplate 100, transparent sealing film 210, temperature controlled heating/cooling platen 230, spacing/alignment blocks 240, and means for clamping 220.

Transparent sealing film 210 is preferably made from a transparent material, such as, but not limited to, polypropylene, acrylic and the like; it should be made sufficiently thin to maintain flexibility.

Spacing/alignment blocks 240 align microplate 100 to the temperature controlled heating/cooling platen, and they also provide consistent height control across the microplate 100 when vertical load is applied onto the microplate 100. They can be made using a structurally stable material, such as, but not limited to, stainless steel.

Means for clamping 220 can include any vertical load application mechanism used to cause the microplate to be pressed down onto the temperature controlled heating/cooling platen 230. One embodiment shown in FIG. 2 consists of a top frame 226, a transparent plate 224, and an elastic layer 222. Top frame 226 is a stiff plate with large rectangular cutout in the center to allow optical access for all microwells 110 in the microplate 100; it is preferably fabricated from stiff material such as, but not limited to, stainless steel. Transparent plate 224, attached to the underside of top frame 226, transfers load from the top frame 226, and distributes it uniformly across the entire top surface of the microplate 100. It is preferably made of stiff material, such as, but not limited to, quartz glass, sapphire and the like. It is surface should be sufficiently planar. Elastic layer 222, attached to the underside of transparent plate 224, distributes load from transparent plate 224 to individual microwell 110. It is preferably fabricated from elastic material, such as, but not limited to, elastomer.

Other embodiment of means for clamping can include a top plate with machined holes aligning with the microwells (this replaces the top frame 226 and transparent plate 224 in previous embodiment). It is preferably to have individual springs attached to the underside of the top plate and they align with machined hole to provide the needed load distribution to the microwells, when vertical load is applied to the top plate. The top plate is preferably fabricated from a stiff material, such as, but not limited to, stainless steel. The springs preferably have an inner diameter slightly larger than the machined hole diameter, it is preferably made from corrosion resistive material, such as, but not limited to, stainless steel.

Figure 3:
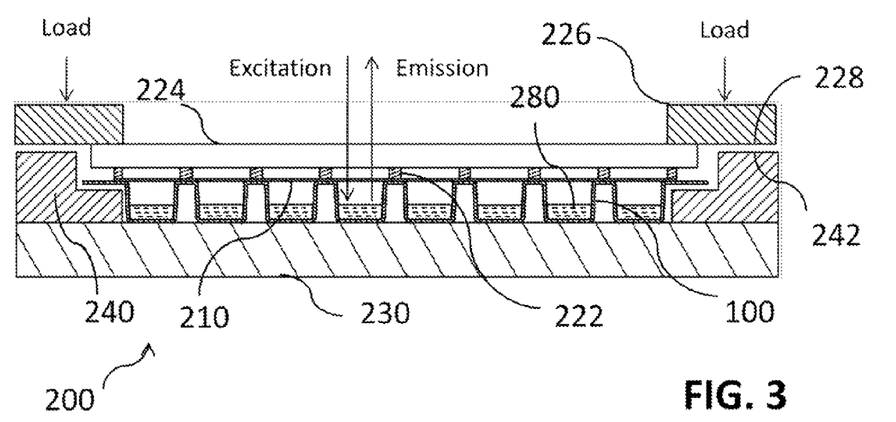
FIG. 3 is a cross-sectional view of the reaction module in FIG. 2.

FIG. 3 shows a cross-sectional view of the reaction module illustrated in FIG. 2, before load is applied to the top frame 226. When load is applied onto top frame 226, the top frame 226 will travel downwards until it is stopped by spacing/alignment blocks 240, at which point the bottom surface 228 of the top frame 226 and the top surface 242 of spacing/alignment blocks 240 are engaged. Load is transferred to the transparent plate 224, and then to the elastic layer 222, which is eventually distributed to each individual microwell 110. Distributed load is transferred further through the microwell side wall 130 which presses the bottom 140 of the microwell against top surface of the temperature controlled heating/cooling platen 230. The amount of loading on individual microwell is determined (and can be tuned) by: the gap between bottom surface 228 of the top frame 226 and the top surface 242 of spacing/alignment blocks 240, elastic layer 222 thickness and material properties, and microplate 100 construction.

Excitation light from an excitation light source is directed downwards towards reaction module 200, it passes through the large cut-out in the center of top frame 226, the transparent plate 224, circular cut outs of the elastic layer 222, and transparent sealing film 210, before reaching liquid samples 280 in the microwells 110. Since the microwells are relative shallow as compared to traditional cone shape design, excitation light can readily penetrate the depth of the liquid samples without much attenuation. Generated fluorescent emission light travels upwards passing the components mentioned above in reverse order and is collected by an optical imaging system.

Figure 4:
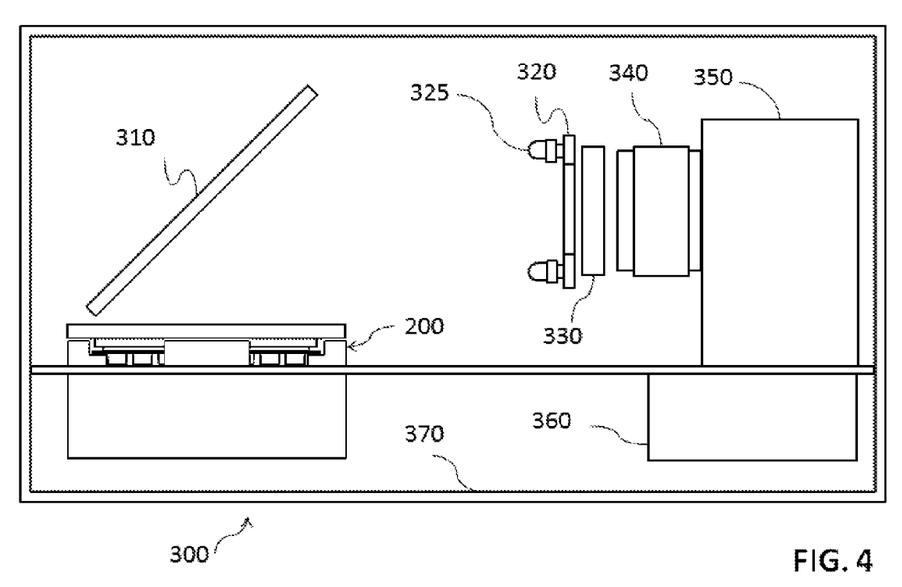
FIG. 4 is a real-time optical detection system that encapsulates a reaction module, first surface mirror, excitation light source, emission filters, optical lens and imaging sensor, power and controlling electronics, as well as other components.

FIG. 4 illustrate one embodiment of fluorescent detection system including reaction module 200, first surface mirror 310, light source assembly 320, emission filter assembly 330, optical lens 340 and imaging sensor 350, power and control electronics 360, and enclosure 370. In this, embodiment, excitation light from light source 320 is directed by the first surface mirror 310 onto the reaction module 200; the generated fluorescent light from the samples travels upwards and is redirected by the first surface mirror 310 towards the emission filter assembly 330, and then collected by optical lens 340 and imaging sensor module 350.

Figure 5:
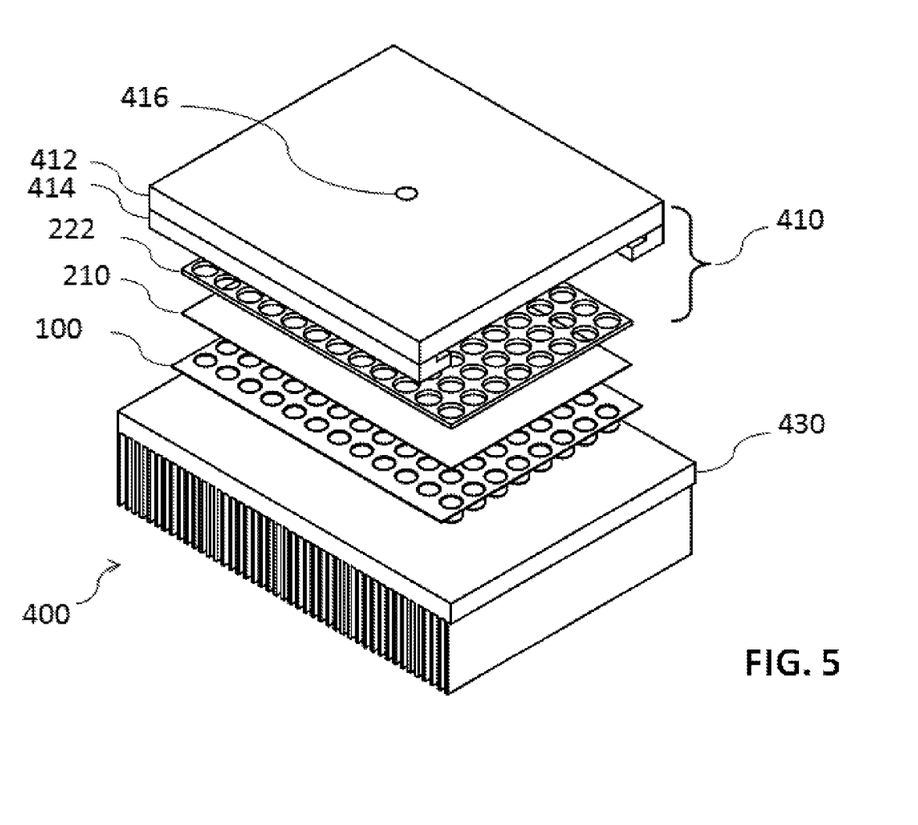
FIG. 5 is an oblique exploded view of another reaction module embodiment according to the invention. The reaction module consists of a top clamping module, a plurality of heating/cooling surfaces (only one shown in this drawing).

FIG. 5 shows another embodiment of reaction module 400 in which there are more than one temperature controlled heating/cooling platens 430 (only one is shown here) set to different temperature profiles/distributions. The temperature controlled heating/cooling platens 430 is interchangeable with other temperature controlled heating/cooling platens. The microplate 100 is configured to engage with the temperature controlled platens dynamically where it attaches and detaches throughout the PCR test process. The reaction module comprises a microplate 100, transparent sealing film 210, temperature controlled heating/cooling platens 430 (only one is shown here), and means for clamping 410. One embodiment of the means for clamping 410 consists of a top frame 412, spacing/alignment blocks 414, and an elastic layer 222. A threaded hole 416 on the top frame 412 is provided to engage vertical transport mechanism.

Figure 6:
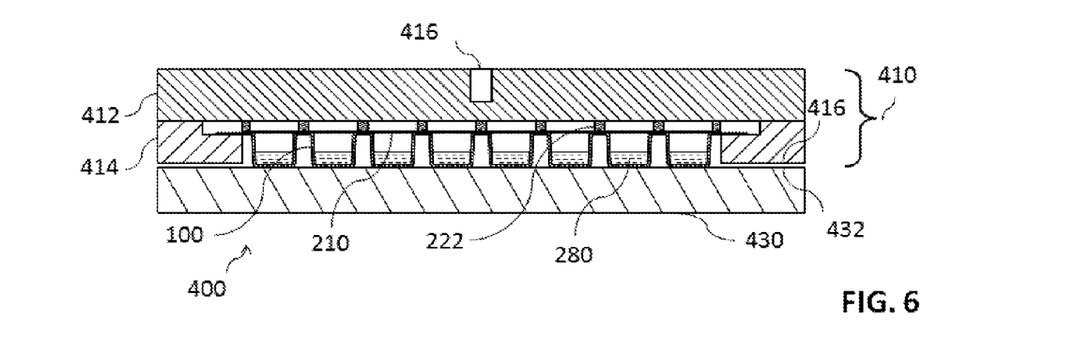
FIG. 6 is a cross-sectional view of reaction module in FIG. 5.

FIG. 6 shows a cross-sectional view of the reaction module shown in FIG. 5, before vertical load is applied to the top frame 412. When load is applied onto top frame 412, means for clamping 410 will travel downwards until it is stopped by temperature controlled heating/cooling platen 430, at which point the bottom surface 416 of the spacing/alignment blocks 414 and the top surface 432 of temperature controlled heating/cooling surfaces 430 are engaged. Vertical load is transferred to the elastic layer 222, which is then distributed to each individual microwell 110. Vertical distributed load is transferred further through the microwell side wall 130 and it presses the bottom of the microwell against the temperature controlled heating/cooling surface 432.

Figure 7:
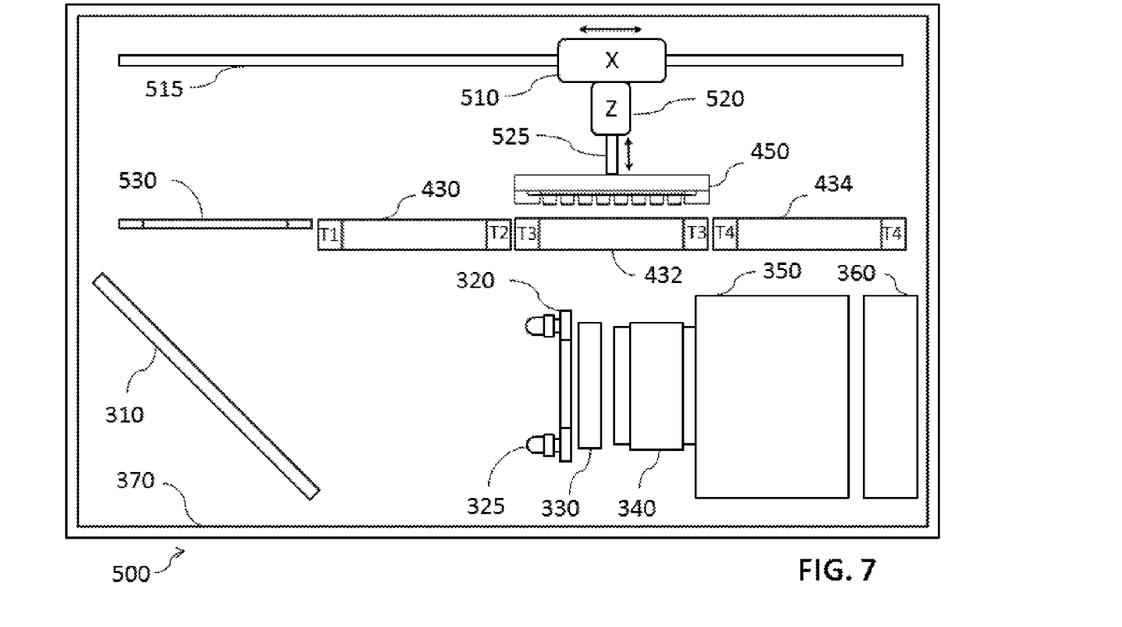
FIG. 7 is a real-time optical detection system that encapsulates a reaction module with a plurality of heating/cooling platens, a first surface mirror, excitation light source assembly, emission filters assembly, optical lens and imaging sensor, power and controlling electronics, as well as other components.

FIG. 7 illustrates one embodiment of fluorescent detection system comprising a reaction module 450, an optical staging plate 530, temperature controlled heating/cooling platens 430, 432, 434, a horizontal servo motor 510 and a horizontal shaft 515, a vertical servo motor 520 and a vertical shaft 525, preferably a first surface mirror 310, a light source assembly 320, an emission filter assembly 330, an optical lens 340 and an imaging sensor 350, power and control electronics 360, and an enclosure 370. The reaction module 450 further comprises of clamping module 410 and microplate 100 and sealing film 210.

In this embodiment, multiple temperature controlled heating/cooling platens 430, 432, 434 set to different temperature profiles are provided, in this example, the first platen 430 has a linear gradient temperature profile going from temperature T1 (90° C., for example) to temperature T2 (98° C., for example) to studying varying denaturation temperature effect; the second platen 432 is set at uniform temperature T3 (50° C., for example) for annealing process; the third platen 434 is set at uniform temperature T4 (70° C., for example) for extension process. It is preferred that the number of temperature controlled heating/cooling platens matches the number of temperature set points of the thermal cycle.

The horizontal servo motor 510 and vertical servo motors 520 are mechanically engaged (for example, vertical servo motor 520 is fixed on horizontal servo motor 510). During test process driven by an automated software program, reaction module 450 is transported by the horizontal servo motor 510 along the horizontal shaft 515 to specific temperature zone, then it is pressed and held against the top surface of one of the temperature controlled platens (430, 432, 434) to allow the chemical reaction to take place by lowering it through the servo motor 520 along the vertical shaft 525, it is then moved to the next temperature surface for next set point in the thermal cycle.

The reaction module can also be transported to the transparent optical staging plate 530, where fluorescent signal can be measured to monitor the progress of the reactions. Excitation light from light source 320 is directed by the first surface mirror 310 onto the reaction module 450 from the bottom; generated fluorescent emission light from the samples travels downwards and is redirected by the first surface mirror 310 towards the emission filter assembly 330, and then collected by optical lens 340 and imaging sensor module 350.

In other embodiments where space constraint is not a concern, the optical imaging module, which includes the light source assembly 320, emission filter assembly 330, optical lens 340 and imaging sensor module 350, could be arranged to directly facing the top surface or bottom surface of the microplate array assembly. In such situation, the first surface mirror 310 can be excluded from the implementation.

Compared to the static embodiment (one temperature controlled heating/cooling platen), this embodiment has the advantage of not having to wait for the temperature controlled heating/cooling platen to transition to next set point temperature, which can speed up test time significantly.

Figure 8A:
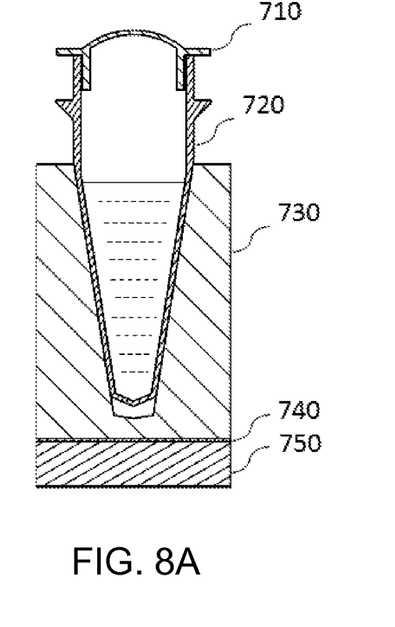
FIG. 8A is a cross-sectional view of microwell with individual sealing cap.
Figure 8B:
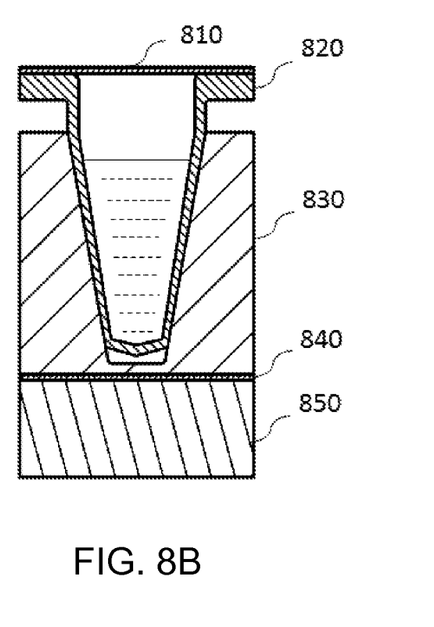
FIG. 8B is a cross-sectional view of microwell covered by a thin transparent film.

FIG. 8A-B show the cross-sectional views of most common state of the art design of microwells and thermal block. FIG. 8A shows a microwell with cone shape body and cylindrical upper portion 720, where the opening is closed by a cap 710 from the top. A thermal block 730 has matching cone shape cavities, and is attached to the temperature control module 750 through a layer of thermal interface material 740. FIG. 8B shows a slightly different implementation where the cap is replaced by a transparent thin film 810 that cover the whole plate top surface. The microwell body 820 has similar cone shape profile, and sample temperature is controlled by a thermal block 830 with matching cavities. The thermal block heating/cooling is provided by the control module 850, attached through a layer of thermal interface material 840.

All publications and patent documents cited in this specification are herein incorporated by reference in their entireties as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the scope of the appended claims.

What is claimed is:

1. A method of facilitating a temperature controlled chemical reaction in a microplate comprising:
   a) providing a microplate comprising a top frame having a planar topside and a plurality of openings defining microwells that hang below and individually comprise side walls and a planar or slightly convex bottom surface, wherein the top frame has flexibility;
   b) providing at least one sample in at least one microwell of said microplate;
   c) sealing off the at least one microwell;
   d) providing a first heating/cooling platen having a temperature control and a rigid planar top surface lacking cavities configured to receive the microwells;
   e) adjusting the temperature control to reach a desired temperature on the top surface of the first heating/cooling platen;
   f) engaging said bottom surfaces of the microplate with the heating/cooling platen's rigid top surface;
   g) providing a means for clamping configured to provide a downward vertical force and applying a vertical load on the topside of the top frame of the microplate, such that the bottom surfaces of the microwells are held flat or substantially so against the rigid planar top surface; and
   h) holding the means for clamping to the microplate assembly for a specific period of time to allow the temperature controlled chemical reaction with the sample to take place.

2. The method of claim 1, further comprising cycling said temperature controlled platen top surface through different thermal cycle temperatures; and emitting fluorescent light through the sample and collecting the fluorescent emission from the sample during each thermal cycle.

3. The method of claim 1, wherein the sample comprises reagents necessary for a Polymerase Chain Reaction (PCR) and undergoes a Polymerase Chain Reaction (PCR).

4. The method of claim 1, wherein said at least one microwell is sealed with an adhesive film that is substantially transparent.

5. The method of claim 1, further comprising:
   a) providing a second heating/cooling platen having a temperature control and a rigid planar top surface lacking cavities configured to receive the microwells;
   b) adjusting the temperature control to reach a desired temperature on the top surface of the second heating/cooling platen that is different from the temperature of the first platen;
   c) disengaging the microplate assembly from said first platen surface;
   d) lowering the microplate such that the microwell bottom surfaces engage with said second platen's rigid top surface;
   d) providing a means for clamping configured to provide a downward vertical force and applying a vertical load on the topside of the top frame of the microplate, such that the bottom surfaces the microwells are held flat or substantially so against the rigid planar top surface of the second platen; and
   e) holding the means for clamping to the microplate assembly for a specific period of time to allow a second temperature controlled chemical reaction with the sample to take place.

6. The method of claim 5, further comprising emitting fluorescent light through the sample after the first and second temperature controlled chemical reactions and collecting the resulting fluorescent emission.

* * * * *